(12) United States Patent
Presura (10) Patent No.: US 7,317,528 B2
(45) Date of Patent: Jan. 8, 2008

(54) ELLIPSOMETER, MEASUREMENT DEVICE AND METHOD, AND LITHOGRAPHIC APPARATUS AND METHOD

(75) Inventor: Cristian Presura, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 38 days.

(21) Appl. No.: 11/183,782

(22) Filed: Jul. 19, 2005

(65) Prior Publication Data

US 2006/0012789 A1 Jan. 19, 2006

Related U.S. Application Data

(63) Continuation of application No. 10/893,542, filed on Jul. 19, 2004.

(51) Int. Cl.
*G01J 4/00* (2006.01)
(52) U.S. Cl. .................. 356/365; 359/494; 359/256
(58) Field of Classification Search ........ 356/364–369; 359/256, 494–496
See application file for complete search history.

(56) References Cited

U.S. PATENT DOCUMENTS

| 3,511,556 | A | * | 5/1970 | Ammann ............... 359/495 |
| 3,902,782 | A | * | 9/1975 | Forman et al. ........... 359/352 |
| 3,914,018 | A | * | 10/1975 | DeShazer ............... 359/496 |
| 4,158,506 | A | * | 6/1979 | Collett ................ 356/365 |
| 5,440,424 | A | * | 8/1995 | Wu et al. ............... 359/495 |
| 6,043,887 | A | * | 3/2000 | Allard et al. ........... 356/364 |
| 6,570,711 | B2 | * | 5/2003 | Ducellier ............... 359/629 |
| 6,794,635 | B2 | * | 9/2004 | Kuerner ............... 250/225 |
| 6,816,261 | B2 | * | 11/2004 | Patel et al. ............ 356/365 |

FOREIGN PATENT DOCUMENTS

| GB | 2352513 | * | 1/2001 |
| JP | 03-167504 A | | 7/1991 |
| JP | 03-287104 | | 12/1991 |
| JP | 05-196567 | | 8/1993 |
| JP | 06-288835 | | 10/1994 |
| JP | 2001-520754 A | | 10/2001 |
| JP | 2002-012977 | | 2/2002 |

OTHER PUBLICATIONS

"Polarization Patent", http://www.instant-analysis.com/patents/polarization_patent.htm dated May 2, 2004.
Translation of Japanese Office Action in JP Appl. No. 2005-235530 Issued Jul. 13, 2007.

* cited by examiner

*Primary Examiner*—Layla G. Lauchman
(74) *Attorney, Agent, or Firm*—Pillsbury Winthrop Shaw Pittman LLP (57) ABSTRACT

An ellipsometer includes an optical component and a detector. The optical component has two birefringent parts in optical communication via a border surface. Light incident on the border surface is split into two reflected and two transmitted components. The detector is configured to measure a property of at least three out of the four components. Based on the measured properties, a state of polarization of the incident light may be determined.

33 Claims, 3 Drawing Sheets

Fig 4

ELLIPSOMETER, MEASUREMENT DEVICE AND METHOD, AND LITHOGRAPHIC APPARATUS AND METHOD

1. RELATED APPLICATIONS

The present invention is a continuation application of application Ser. No. 10/893,542 filed Jul. 19, 2004, the entire contents of which are hereby incorporated by reference.

2. FIELD OF THE INVENTION

The present invention relates to lithographic apparatus and methods.

3. BACKGROUND

A lithographic apparatus is a machine that applies a desired pattern onto a target portion of a substrate. Lithographic apparatus can be used, for example, in the manufacture of integrated circuits (ICs). In that circumstance, a patterning structure, such as a mask, may be used to generate a circuit pattern corresponding to an individual layer of the IC, and this pattern can be imaged onto a target portion (e.g. including part of, one or several dies) on a substrate (e.g. a silicon wafer) that has a layer of radiation-sensitive material (resist). In general, a single substrate will contain a network of adjacent target portions that are successively exposed. Known lithographic apparatus include so-called steppers, in which each target portion is irradiated by exposing an entire pattern onto the target portion all at once, and so-called scanners, in which each target portion is irradiated by scanning the pattern through the projection beam in a given direction (the "scanning"-direction) while synchronously scanning the substrate parallel or anti-parallel to this direction.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist) or a metrology or inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The terms "radiation" and "beam" used herein encompass all types of electromagnetic radiation, including radiation outside the visible range (i.e. 380-780 nm), ultraviolet (UV) radiation (e.g. having a wavelength of 365, 248, 193, 157 or 126 nm) and extreme ultra-violet (EUV) radiation (e.g. having a wavelength in the range of 5-20 nm), as well as particle beams, such as ion beams or electron beams.

The term "patterning structure" used herein should be broadly interpreted as referring to a structure that can be used to impart a beam of radiation with a pattern in its cross-section such as to create a pattern in a target portion of the substrate. It should be noted that the pattern imparted to the beam of radiation may not exactly correspond to the desired pattern in the target portion of the substrate. Generally, the pattern imparted to the beam of radiation will correspond to a particular functional layer in a device being created in the target portion, such as an integrated circuit.

Patterning structures may be transmissive or reflective. Examples of patterning structures include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions; in this manner, the reflected beam is patterned.

The support structure supports, i.e. bears the weight of, the patterning structure. It holds the patterning structure in a way depending on the orientation of the patterning structure, the design of the lithographic apparatus, and other conditions, such as for example whether or not the patterning structure is held in a vacuum environment. The support can use mechanical clamping, vacuum, or other clamping techniques, for example electrostatic clamping under vacuum conditions. The support structure may be a frame or a table, for example, which may be fixed or movable as required and which may ensure that the patterning structure is at a desired position, for example with respect to the projection system. Any use of the terms "reticle" or "mask" herein may be considered synonymous with the more general term "patterning structure".

The term "projection system" used herein should be broadly interpreted as encompassing various types of projection system, including refractive optical systems, reflective optical systems, and catadioptric optical systems, as appropriate for example for the exposure radiation being used, or for other factors such as the use of an immersion fluid or the use of a vacuum. Any use of the term "lens" herein may be considered as synonymous with the more general term "projection system".

The illumination system may also encompass various types of optical components, including refractive, reflective, and catadioptric optical components for directing, shaping, or controlling the projection beam of radiation, and such components may also be referred to below, collectively or singularly, as a "lens".

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein the substrate is immersed in a liquid having a relatively high refractive index, e.g. water, so as to fill a space between the final element of the projection system and the substrate. Immersion liquids may also be applied to other spaces in the lithographic apparatus, for example, between the mask and the first element of the projection system. Immersion techniques are well known in the art for increasing the numerical aperture of projection systems.

Ellipsometers are typically used for determining the complex reflectivity of a surface. Such a surface may be, for example, the top of a wafer, an alignment marker/structure on a wafer, or a piece of human tissue. Interpretation of the measured complex reflectivity yields information about the properties of the respective surface.

Existing apparatuses allow for only one-dimensional measurements, the inventors note that it may be possible in the future to perform measurements in two dimensions, enabling to determine mutual distances between, for example, alignment markers. Ellipsometers may thus be used in a lithographic apparatus. In particular, ellipsometers are employed in connection with (wafer) alignment.

Presently available ellipsometers (also named scatterometers) are generally slow. This slowness may cause a long measurement time in any application, and it may be a critical problem for in-line metrology applications for scatterometers. This long measurement time is generally primarily related to the technical design of the measurement unit of an ellipsometer. Typically, the measurement of the elliptical polarized light is done using measurement devices that include moveable parts such as rotating analyzers, or rotating retarders. Also, photo-elastic modulators are commonly used. These photo-elastic modulators can also be considered as measurement devices containing moveable parts.

An example of an ellipsometer can be found, for example, at http://www.instant-analysis.com/patents/polarization_patent_new.htm (as available on May 2, 2004). This document discloses a special analyzing plate consisting of four polarizers in different positions covering six photo detectors and a waveplate that covers two photo detectors. Monochromatic light is incident on the analyzing plate and subsequently hits the photo detectors. The electric signals generated by the incident light on the photo detectors are used, in conjunction with a suitable computer, to measure the polarization state of the monochromatic light incident on the analyzing plate. To assess the polarization state of the monochromatic light, it is desirable to obtain information about the degree-of-polarization, azimuth angle and ellipticity of the monochromatic light. The analyzing mask as described above, however, and the number of required detectors, makes this ellipsometer relatively complex. A minimum number of four detectors may be required in a conventional ellipsometer.

4. SUMMARY

An ellipsometer according to one embodiment of the invention includes an optical component including at least a first part being connected along a border surface to a second part, the first part and the second part being birefringent. The first part has a first optical axis oriented along a first direction and the second part has a second optical axis oriented along a second direction, the first direction being different from the second direction. The optical component is arranged in use to receive a beam of radiation on the border surface, the beam having a state of polarization. The border surface is arranged to split the beam into a first and a second component which are, when the ellipsometer is in use, reflected into the first part and a third and a fourth component which are, when the ellipsometer is in use, transmitted into the second part. The at least one detector is arranged to measure a property of at least three out of the four components to allow calculating the state of polarization. In one application, such a device is used to enable a swift measurement of the state of polarization of incident light.

An ellipsometer according to another embodiment of the invention, includes at least one optical component including at least a first birefringent part and a second birefringent part, the first birefringent part having a first optical axis oriented along a first direction and being connected along a border surface to the second birefringent part, the second birefringent part having a second optical axis oriented along a second direction different from the first direction. The ellipsometer also includes at least one detector. The at least one optical component is configured to receive a beam of radiation, having a state of polarization, on the border surface, and the border surface is configured to split the beam into a first and a second component reflected into the first birefringent part and to split the beam into a third and a fourth component transmitted into the second birefringent part. The at least one detector is configured to measure a property of at least three out of the four components to calculate the state of polarization.

In an embodiment of the invention, there is provided a measurement device including an ellipsometer as described above and a detection and evaluation unit configured to calculate the state of polarization.

A device manufacturing method according to an embodiment of the invention includes providing a substrate; providing a beam of radiation using an illumination system; using a patterning structure to impart the beam of radiation with a pattern in its cross-section; and projecting the patterned beam of radiation onto a target portion of the substrate, wherein an ellipsometer as described above is used to characterize a surface of the substrate.

A device manufacturing method according to another embodiment includes determining the complex reflectivity of a surface of a substrate; providing a beam of radiation; patterning the beam of radiation; and projecting the patterned beam of radiation onto a target portion on the surface of said substrate, wherein the determination of the complex reflectivity of the surface is done with an ellipsometer as described herein.

A device manufacturing method according to a further embodiment of the invention includes providing a substrate; providing a beam of radiation using an illumination system; using a patterning structure to impart the beam of radiation with a pattern in its cross-section; and projecting the patterned beam of radiation onto a target portion of the substrate, wherein a measurement device as described above is used to characterize a surface of the substrate.

A method according to an embodiment includes providing a beam of radiation; patterning the beam of radiation with a pattern in its cross-section; projecting the patterned beam of radiation onto a target portion of a surface of a substrate, and measuring a complex reflectivity of the surface of the substrate using a measurement device as described herein.

A method of measurement according to an embodiment of the invention includes directing a measurement beam of radiation along an optical axis of a first birefringent part to a border surface between the first birefringent part and a second birefringent part, the second birefringent part having an optical axis oriented along a different direction from the optical axis of the first birefringent part. The method also includes measuring a property of each of at least three components of a group comprising first and second components of the measurement beam reflected from the border surface into the first birefringent part and third and fourth components of the measurement beam transmitted from the border surface into the second birefringent part.

An ellipsometer according to another embodiment of the invention includes a first birefringent part, a second birefringent part, and at least one detector. The first and second birefringent parts are arranged in optical communication via a border surface such that a beam of radiation transmitted through said first birefringent part is split into a first component, a second component, a third component, and a fourth component, said first and second components being reflected from said border surface into said first birefringent part and the third and fourth components being transmitted from the border surface into the second birefringent part. The at least one detector is configured to measure a property of each of at least three of the first, second, third and fourth components.

5. BRIEF DESCRIPTION OF THE DRAWINGS

Embodiments of the invention will now be described, by way of example only, with reference to the accompanying schematic drawings in which corresponding reference symbols indicate corresponding parts, and in which.

6. DETAILED DESCRIPTION

Embodiments of the present invention include an ellipsometer with improved design characteristics (i.e. a relatively simple ellipsometer) that is configured to measure a polarization state of incoming monochromatic light in a swift, easy and reliable way using only a minimum number of detectors.

Figure 1:
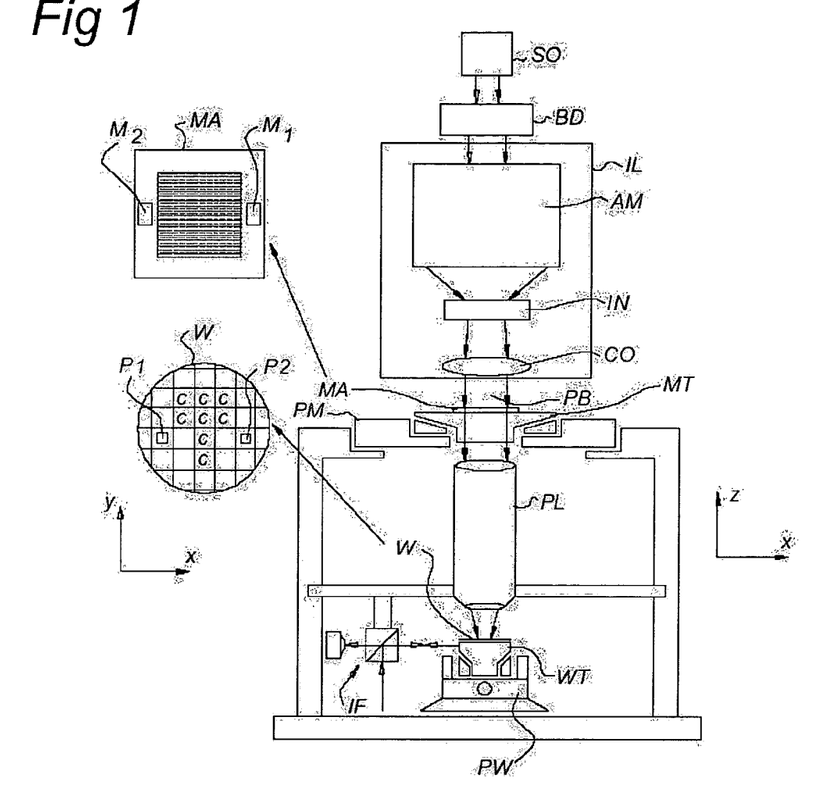
FIG. 1 depicts a lithographic apparatus according to an embodiment of the invention.

FIG. 1 schematically depicts a lithographic apparatus according to an embodiment of the invention. The apparatus includes an illumination system (illuminator) IL configured to provide a beam PB of radiation (e.g. UV radiation or EUV radiation), a first support structure (e.g. a mask table) MT configured to support a patterning structure (e.g. a mask) MA and connected to first positioning device PM configured to accurately position the patterning structure with respect to a projection system ("lens"), item PL. The apparatus also includes a substrate table (e.g. a wafer table) WT configured to hold a substrate (e.g. a resist-coated wafer) W and connected to a second positioning device PW configured to accurately position the substrate with respect to the projection system ("lens"), item PL, the projection system (e.g. a refractive projection lens) PL being configured to image a pattern imparted to the projection beam PB by the patterning structure MA onto a target portion C (e.g. comprising one or more dies) of the substrate W.

As here depicted, the apparatus is of a transmissive type (e.g. employing a transmissive mask). Alternatively, the apparatus may be of a reflective type (e.g. employing a programmable mirror array of a type as referred to above).

The illuminator IL receives a beam of radiation from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including for example suitable directing mirrors and/or a beam expander. In other cases the source may be an integral part of the apparatus, for example when the source is a mercury lamp. The source SO and the illuminator IL, together with the beam delivery system BD if required, may be referred to as a radiation system.

The illuminator IL may include an adjusting structure AM configured to adjust the angular intensity distribution of the beam. Generally, at least the outer and/or inner radial extent (commonly referred to as σ-outer and σ-inner, respectively) of the intensity distribution in a pupil plane of the illuminator can be adjusted. In addition, the illuminator IL generally includes various other components, such as an integrator IN and a condenser CO. The illuminator provides a conditioned beam of radiation, referred to as the beam of radiation PB, having a desired uniformity and intensity distribution in its cross-section.

The beam of radiation PB is incident on the mask MA, which is held on the mask table MT. Having traversed the mask MA, the beam of radiation PB passes through the lens PL, which focuses the beam onto a target portion C of the substrate W. With the aid of the second positioning device PW and position sensor IF (e.g. an interferometric device), the substrate table WT can be moved accurately, e.g. so as to position different target portions C in the path of the beam PB. Similarly, the first positioning device PM and another position sensor (which is not explicitly depicted in FIG. 1) can be used to accurately position the mask MA with respect to the path of the beam PB, e.g. after mechanical retrieval from a mask library, or during a scan. In general, movement of the object tables MT and WT will be realized with the aid of a long-stroke module (coarse positioning) and a short-stroke module (fine positioning), which form part of the positioning device PM and PW. However, in the case of a stepper (as opposed to a scanner) the mask table MT may be connected to a short stroke actuator only, or may be fixed. Mask MA and substrate W may be aligned using mask alignment marks M1, M2 and substrate alignment marks P1, P2.

The depicted apparatus can be used in the following preferred modes:

1. In step mode, the mask table MT and the substrate table WT are kept essentially stationary, while an entire pattern imparted to the beam of radiation is projected onto a target portion C at once (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the beam of radiation is projected onto a target portion C (i.e. a single dynamic exposure). The velocity and direction of the substrate table WT relative to the mask table MT is determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning structure, and the substrate table WT is moved or scanned while a pattern imparted to the projection beam is projected onto a target portion C. In this mode, generally a pulsed radiation source is employed and the programmable patterning structure is updated as required after each movement of the substrate table WT or in between successive radiation pulses during a scan. This mode of operation can be readily applied to maskless lithography that utilizes programmable patterning structures, such as a programmable mirror array of a type as referred to above.

Combinations and/or variations on the above described modes of use or entirely different modes of use may also be employed.

Figure 2:
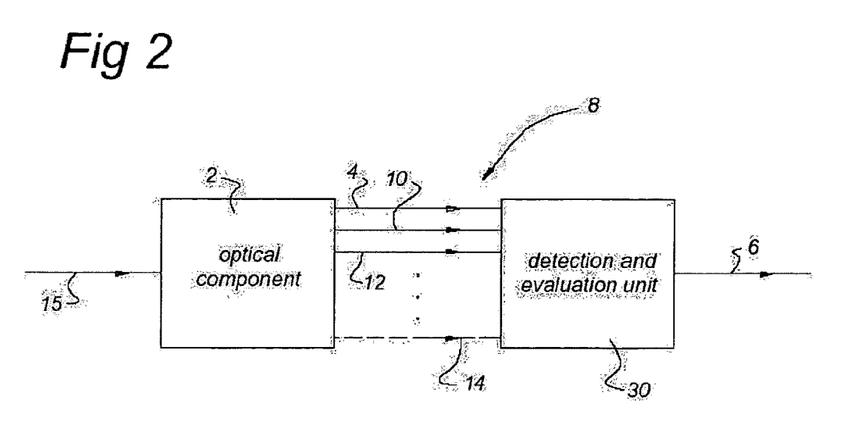
FIG. 2 shows a principle of operation of an ellipsometer.

With reference to FIG. 2, a general principle of operation of an ellipsometer 8 is explained. Such an ellipsometer 8 may be present, for example, near the wafer stage in a lithographic apparatus (see FIG. 1) or in the alignment unit of a dual stage scan apparatus. The ellipsometer 8 includes an optical component (or combination of optical components), shown schematically as a rectangle indicated by reference numeral 2. A monochromatic beam of light 15 enters the optical component 2. The beam 15 may be received from a surface under investigation. In the optical component 2, a set of measurements may be carried out with different combinations of polarizers and/or waveplates in different subsequent positions. Obtaining such measurements may require physical movements of these components, which may be a time consuming operation. Alternatively, it is also possible to split the beam 15 in several components that pass through combinations of polarizers and/or waveplates at the same time. However, this may render an ellipsometer based on this principle relatively complex.

Either such method may be used to provide measurement signals (e.g. from one or more photo detectors receiving the beam and/or components thereof) as referred to with respective reference numerals 4, 10, 12 and 14 in FIG. 2. The measurement signals 4, 10, 12 and 14 are input to a detection and evaluation unit 30. The detection and evaluation unit 30 (which may include, for example, a number of photo detectors and/or a suitably programmed computer or processor) evaluates the measurement signals 4, 10, 12 and 14 and provides the state of polarization 6 of the incoming beam 15.

Figure 3:
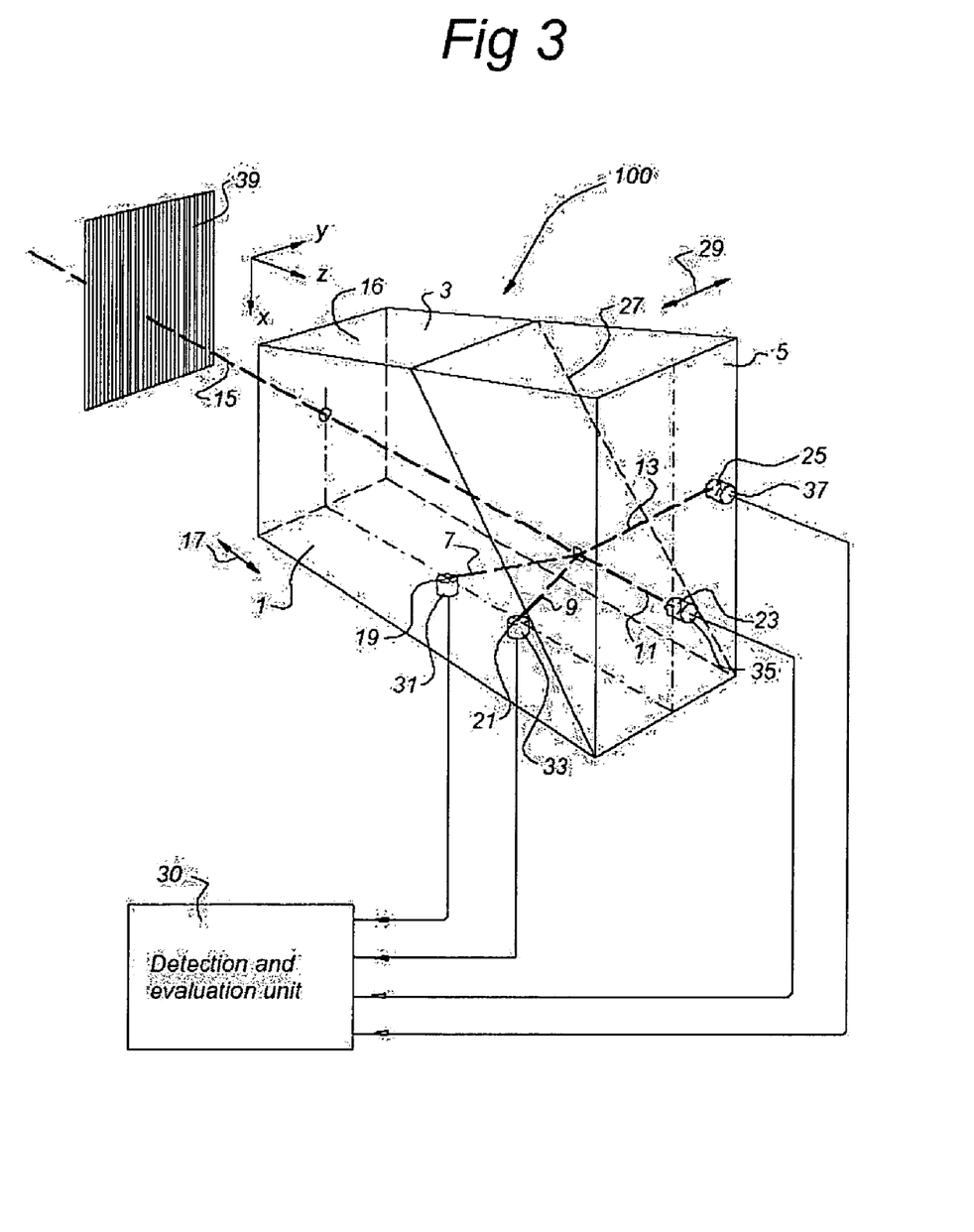
FIG. 3 shows an ellipsometer according to an embodiment of the present invention.

In FIG. 3, an ellipsometer 100 according to an embodiment of the present invention is shown. Similar reference numerals as used in connection with FIG. 2 refer to similar parts. The ellipsometer in FIG. 3 includes a prism 1. This prism 1 may be employed as the optical component 2 in FIG. 2. The prism 1 includes a first part 3 and a second part 5. The first part 3 has an uniaxial (or "optic" or "optical") axis 17 and the second part 5 has an uniaxial axis 29.

The first part 3 and the second part 5 are connected to each other along a border surface or border surface 27. It will be appreciated that the term "connected" as used herein to indicate a relation between the first part and the second part does not necessarily refer to a fixed connection. It should be understood that the first part 3 and the second part 5 may be placed in each other's vicinity (e.g. such that optical communication from the first part to the second part may occur). At the border surface 27, the monochromatic beam 15 of light is split into four parts or components 7, 9, 11 and 13 that hit four respective detectors 31, 33, 35 and 37 located at respective locations 19, 21, 23 and 25. The detectors 31, 33, 35 and 37 are connected to the detection and evaluation unit 30.

The ellipsometer functions in the following way. The prism 1 is oriented in such a way that the uniaxial axis 17 of the first part 3 is substantially along the direction of propagation of the incoming monochromatic beam 15. Such orientation may require a suitable calibration beforehand. The beam 15 may include visible light and/or radiation with a frequency outside (e.g. above or below) the visible part of the electromagnetic spectrum. The beam 15 impinges on a front surface or "face" 16 of prism 1 and enters the prism 1. The front surface 16 and the border surface 27 are oriented at a predetermined angle with respect to each other.

As the beam 15 is directed substantially along the uniaxial axis 17, it will remain substantially unsplit while passing through the first part 3. When the beam 15 hits the border surface 27, parts 11 and 13 of the beam 15 will be transmitted to the second part 5 of the prism 1, and parts 7 and 9 of the beam 15 will be reflected backwards into the first part 3. The orientation of the uniaxial axis 17 of the first part 3 of the prism 1 is different from the orientation of the uniaxial axis 29 of the second part 5 of the prism 1. The second part 5 may be positioned in such a way with respect to the first part 3 that the transmitted beam 11 will be exactly aligned with the beam 15. However, principles of the invention may also be applied to arrangements in which this particular alignment is not present.

The part 3 and the part 5 are birefringent. This means, as will be apparent to the skilled person, that the beam 15 after being reflected by the border surface 27 will propagate at an angle relative to the uniaxial axis 17, and will be split in two linearly polarized states that are mutually orthogonal, an ordinary or "o"-part 9 and an extraordinary or "e"-part 7. The transmitted part of the beam 15 at the border surface 27 will be at an angle relative to uniaxial axis 29 and is split into an ordinary or "o"-part 11 and an extraordinary or "e"-part 13. The definitions of "ordinary" and "extraordinary" are known to the skilled person.

The parts 7, 9, 11 and 13 subsequently hit the four respective detectors 31, 33, 35 and 37 located at respective locations 19, 21, 23 and 25. These detectors 31, 33, 35 and 37 measure the intensities of the parts 7, 9, 11 and 13. They send output signals indicating these four intensities to the detection and evaluation unit 30. This unit may be constructed as an evaluation unit comprising, e.g., a processor configured to evaluate expressions as described herein. From the intensities and the polarization of the o- and e-parts, the detection and evaluation unit 30 determines the polarization of the incoming beam 15 in accordance with calculation rules known to the skilled person. The o-part 9 is y polarized at 0° compared with the beam 15, the e-part 7 is (x+y) polarized at 900 compared with the beam 15, the o-part 11 is (x−y) polarized at −45° compared with the beam 15 and the e-part 13 is (x+y) polarized at 45° compared with the beam 15. Alternatively, the phase of the parts 7, 9, 11 and 13 of the beam 15 may be used, instead of (and/or in addition to) the intensities, to obtain the state of polarization of the beam 15.

In addition, the border surface 27 may be coated with a suitable substance to equalize the transmitted and reflected optical power, i.e. to divide the total input power of beam 15 over the reflected beams 7, 9 and the transmitted beams 11, 13 (such as, e.g. 50%-50%) such that all beams have enough power to allow easy detection. For example, a TBP reflective coating (a broadband partially reflective coating that reflects up to 50%, e.g. as marketed by LINOS Aktiengesellschaft, Goettingen, Del.) may be used.

Also, as a "fill up" material at the location of the border surface 27 (a layer of) air may be considered. In an embodiment of the invention, the resulting "air gap" may be in the order of half the wavelength used (e.g. a few hundred nanometers) in between the first part 3 and the second part 5. In such case, there may be no direct mechanical contact between first part 3 and the second part 5.

In another embodiment of the invention, air may be combined with a coating. For example, one may fill the gap in between the first part 3 and the second part 5, partly, e.g. with a substance such a TBP reflective coating mentioned above, combined with an air gap of about 5 micrometer. In this case, it may be desirable to avoid mechanical contact between the first part 3 and the second part 5, since e.g. mechanical contact may cause stresses in the substance/coating that may deform it and/or have an effect on properties (e.g. of reflection) of the coating.

For purpose of illustration, an example is given below describing how the polarization of an incoming beam of radiation 15 can be calculated from the intensities measured by the detectors 31, 33, 35 and 37 (see also FIG. 3).

With reference to the prism 1, as shown in FIG. 3, the axes $\{x,y,z\}$ are also indicated. Elliptically polarized light incident on the face 16 is given by two components in the $\{xy\}$ plane:

$$E_x = E_a \sin(\omega t)$$

$$E_y = E_b \sin(\omega t + \delta)$$

In principle, the above relation states that elliptically polarized light can be seen as a sum of two linearly polarized beams, which have a phase difference $\delta$ and an amplitude ratio R:

$$R = \frac{E_a}{E_b}.$$

The ellipsometer may be applied to measure R and $\delta$.

In complex terms, the two incident amplitudes may be written as:

$$E_x = E_a e^{j\omega t}$$

$$E_y = E_b e^{j(\omega t + \delta)}$$

where $j = \sqrt{-1}$. These beams "travel" unchanged until the border surface 27. There, parts 7, 9 of the incident beam 15 are reflected and parts 11, 13 are transmitted. First the reflected parts 7, 9 are considered.

If the border surface 27 is coated, the reflection at the coated border surface 27 may be described by a reflection coefficient r. This coefficient is a property of the coating, and depends usually on the orientation of the polarization of the light and the incident angle. In addition, the reflection coefficient is a complex number.

Due to the particular orientation of the axis 17 of the first part 3 of the prism 1, it can be seen that the part 9 of the incident beam 15, also referred to below as ON (polarization perpendicular on the plane of incidence) is the ordinary beam, and the part 7, also referred to below as OM (polarization in the plane of incidence) is the extraordinary beam. The reflection coefficients of the coating at the border surface 27 for the ON (initially 0°, or y component) and OM (initially 90°, or x component) parts are taken as $r_0$ and $r_{90}$.

The amplitudes of the OM and ON parts become then:

$$E_{OM} = r_{90} E_a e^{j\omega t}$$

$$E_{ON} = r_0 E_b e^{j(\omega t + \delta)}$$

and the intensities of the two parts 7, 9 are given by:

$$I_M = |r_{90}|^2 E_a^2$$

$$I_N = |r_0|^2 E_b^2.$$

Here (see FIG. 3) $I_M$ refers to the intensity of part 7 as measured by the detector 31 and $I_N$ refers to the intensity of part 9 as measured by the detector 33. The first R value can then be calculated as:

$$R = \frac{E_a}{E_b} = \left|\frac{r_0}{r_{90}}\right| \sqrt{\frac{I_M}{I_N}} \quad (1)$$

It should be noted that only the absolute reflection coefficients of the coated material at the border surface 27 enter into the formula (1) in the example above.

In order to calculate $\delta$, the transmitted parts 11, 13 of the beam 15, and R, which can be calculated from the relation as derived above, may be used.

The second part 5 of the prism 1 may be oriented in such a way as to choose the polarization of the transmitted ordinary beam 11 (also referred to below as OR) in the x+y direction to be −45° and the one of the extraordinary beam 13 (also referred to below as OS) in the −x+y direction to be 45°. In such a case, the orientation of the optical axis 29 can be determined considering that it must be perpendicular to the polarization of the ordinary axis (which is x+y). Thus, it must be confined in the plane determined by the vectors (x−y) and (z). One reasonable option is the direction (x−y+z).

The coating layer 27 also has some transmission coefficients, which are dependent as well on the polarization and angle of incidence, and also are complex numbers. In this example, only the numbers that present interest are used, namely $t_{+45}$ and $t_{−45}$. Here, $t_{+45}$ refers to the transmission coefficient of the part 13 of the beam 15 polarized at 45° and $t_{−45}$ refers to the transmission coefficient of the part 11 of the beam 15 polarized at −45°.

Then, the amplitudes of the transmitted parts 11, 13, also referred to below as OR and OS, respectively, can be written as:

$$E_{OR} = t_{-45} E_{-45}$$

$$E_{OS} = t_{+45} E_{+45}.$$

This gives the intensities:

$$I_R = |t_{-45}|^2 E_{-45}^2$$

$$I_S = |t_{45}|^2 E_{45}^2.$$

Figure 4:
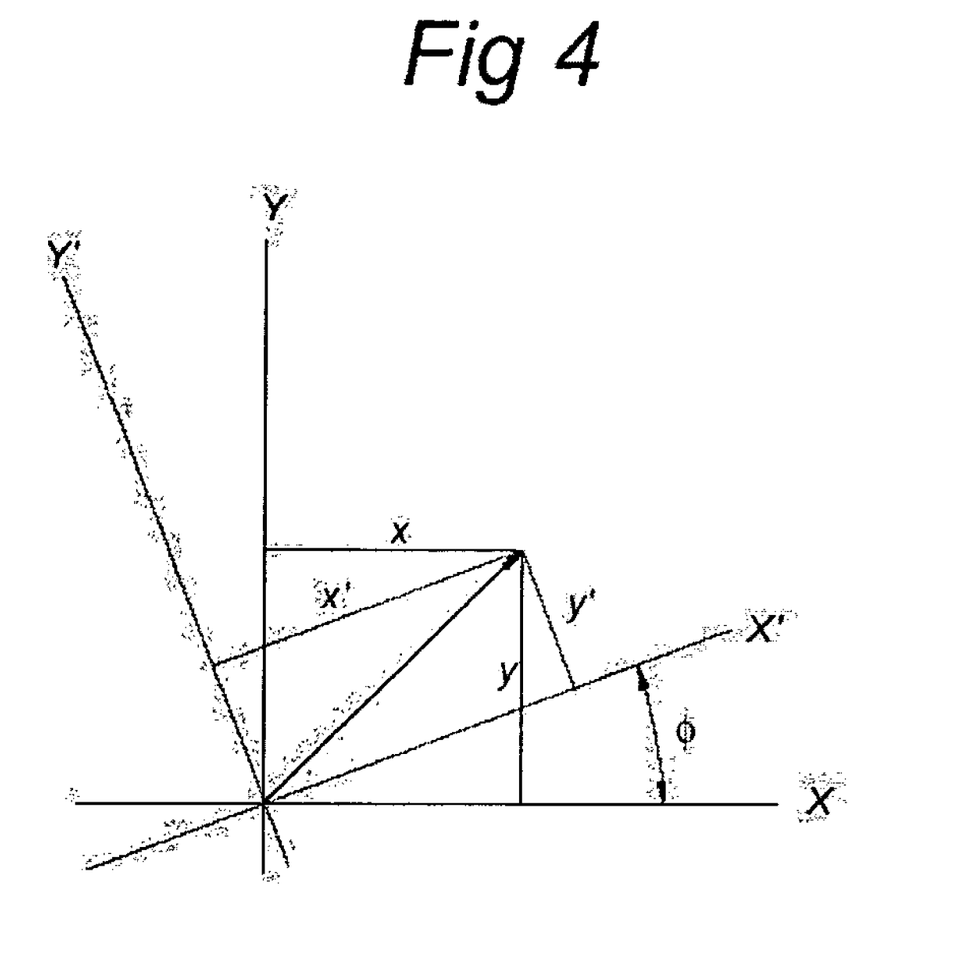
FIG. 4 is a graphic representation of a matrix of rotation according to an embodiment of the invention.

Here, see FIG. 3, $I_R$ refers to the intensity as measured by the detector 35 and $I_S$ refers to the intensity as measured by the detector 37. The components for the incident fields at the interface $E_{+45}$, $E_{-45}$, are not written here explicitly because they are calculated from the known incident fields $E_a$, $E_b$, and the corresponding phase $\delta$. This can be done using a matrix of rotation, as shown in FIG. 4.

The matrix is written as:

$$\begin{bmatrix} E_{+45} \\ E_{-45} \end{bmatrix} = \begin{bmatrix} \cos(45°) & \sin(45°) \\ -\sin(45°) & \cos(45°) \end{bmatrix} \begin{bmatrix} E_x \\ E_y \end{bmatrix} = \begin{bmatrix} E_x + E_y \\ -E_x + E_y \end{bmatrix},$$

in which a factor of ½ √2 has been omitted in front of the right hand matrix, as it cancels in the ratio of the intensities on the detectors 35 and 37, written as:

$$\frac{I_R}{I_S} = \left|\frac{t_{-45}}{t_{45}}\right|^2 \left|\frac{E_{-45}}{E_{45}}\right|^2 = \left|\frac{t_{-45}}{t_{45}}\right|^2 \left|\frac{-E_x + E_y}{E_x + E_y}\right|^2.$$

The complex initial formulas for $E_x$ and $E_y$ are now replaced to obtain:

$$\frac{I_R}{I_S} = \left|\frac{t_{-45}}{t_{45}}\right|^2 \left|\frac{-E_a e^{j(\omega t)} + E_b e^{j(\omega t+\delta)}}{E_a e^{j(\omega t)} + E_b e^{j(\omega t+\delta)}}\right|^2 = \left|\frac{t_{-45}}{t_{45}}\right|^2 \left|\frac{-R + e^{j\delta}}{E + e^{j\delta}}\right|^2$$

which may be further simplified as:

$$\frac{I_r}{I_s} = \left|\frac{t_{-45}}{t_{45}}\right|^2 \frac{R^2 - 2R\cos\delta + 1}{R^2 + 2R\cos\delta + 1}$$

For the above formula one finds immediately the value of the phase difference $\delta$:

$$\cos\delta = \frac{R^2 + 1}{2R} \frac{R' - 1}{R' + 1} \qquad (2)$$

where:

$$R' = \frac{I_S}{I_R}\left|\frac{t_{-45}}{t_{45}}\right|^2.$$

It should be noted that, in the above calculations, real numbers have been used for the reflection coefficients and transmission coefficients. In general, however, these coefficients may as well be tensors. Hence, these coefficients may be matrices. Then, the result will not be given by the formulas (1) and (2) above, but by a system of equations which must be solved accordingly. Formulas (1) and (2) in this case are only approximations.

It can thus be seen that the properties of the elliptically polarized light (R and $\delta$) can be measured using formula (1) for R and formula (2) for $\delta$, once the transmission t and reflection r coefficients of the coating are known, and if the intensities of all four detectors 31, 33, 35 and 37 are measured, to calculate the ratios $I_M/I_N$ and $I_S/I_R$. It is even possible to dispense with one detector and use a total number of three detectors to obtain the properties of the elliptically polarized light.

To explain this idea further, reference is again made to FIG. 4. Let us suppose that we have only three detectors, corresponding to polarizations along the X-, Y-, and X'-directions (beams 7, 9, and 11). In the following, the values of the reflection coefficients or transmission coefficients are not taken into account. The ratio of the intensities, as measured by a first detector corresponding to the X direction and a second detector corresponding to the Y direction, gives one parameter of the ellipse, namely: R=Ex/Ey=$\sqrt{}$(Ix/Iy), see formula (1). The incoming elliptically polarized light is a coherent combination of two linearly polarized beams, one along the X-direction and one along the Y-direction. The ratio Ex/Ey of the amplitudes is one parameter calculated in ellipsometry.

In order to completely characterize the elliptically polarized beam, however, the phase between the two linearly polarized components Ex and Ey is needed as well. But the phase difference cannot be determined by measuring only the intensities Ix and Iy. This can be seen by observing that by changing the phase difference between the two linearly polarized components Ex and Ey, the intensities Ix and Iy remain the same. However, the intensity measured along a different direction (such as X') may change. For example, let us consider the case Ex=Ey. If the phase difference between Ex and Ey is 0, then linearly polarized light along X' is obtained (if X' is oriented at 45 degrees with respect to X, see FIG. 4), and thus Ex'=$\sqrt{}$(2)Ex. If the phase difference between Ex and Ey is 180 degrees, light polarized along Y' is obtained and thus Ex'=0. In other words, Ex' varies from 0 to $\sqrt{}$2)Ex according to the phase difference between Ex and Ey, and this can be measured with a third detector measuring the intensity along the direction X'.

While in the above description, the intensity has been used as a measured quantity, the same properties of the ellipticity can be obtained when using the phase as a measured quantity. To measure the phases, it may be desirable to mix up the reflected and transmitted beams 7, 9, 11, 13, and create thus effectively an interferometer. This result can be realized for example by feeding up the beams 11 and 13 into a single detector, after the polarization of beam 11 has been rotated 90 degrees, with, for example, a half wave plate.

The angle between the front face 16 on which beam 15 is incident and the border surface 27 can be designed such that the angle between the o-part 9 and the e-part 7 is maximized. In that configuration, the distance between the detectors 31, 33 can be relatively large. This predetermined angle may vary largely with tens of degrees. A mathematical relation between the predetermined angle and the angle between the o- and e-parts exists. However, a typical interval for the angle is 0°-30° (for a prism 1 made of calcite), resulting in a split between the o- and e-parts of 5° to 15°.

If the first part 3 and the second part 5 are placed one on top of the other, the reflected part 9 and 7 of the beam 15 may have a low intensity, e.g. less than 10%. This may be valuable in some cases, e.g. if the beam 15 is polarized in the shape of an elongated ellipse. In this case, the prism 1 may be adjusted to have about the same intensity on the four detectors 31, 33, 35 and 37. For example, adjustments can be made to the coating used and/or to the angles of the prism 1.

It will be appreciated that only three intensities may be sufficient to calculate the polarization of the incoming beam 15. However, the fourth intensity, which may also be obtained, can be used for calibration or error control purposes (e.g. misalignment of the incoming beam 15 with reference to the uniaxial axis 17). A relation, namely that the sum of the four intensities measured equates to some constant, exists among the four intensities as measured irrespective of the polarization of the incoming beam 15.

It will be appreciated that an ellipsometer according to an embodiment of the invention can be used to perform broadband measurements, e.g. using a grating in front of a detector. A grating 39 may be present in front of the face 16 as shown in FIG. 3. Additionally, or alternatively, a grating may be positioned in front of one or more of the individual detectors 31, 33, 35 and 37.

The size of the prism 1 may be in the order of centimeters in an embodiment of the invention. It will be appreciated that an ellipsometer according to an embodiment as described herein may be employed in both lithographic apparatus of a transmissive type (see FIG. 1) and of a reflective type.

According to an embodiment of the invention, at least one of a phase and an intensity of a component is measured. The phase and the intensity are properties from which the state of polarization may be easily obtained.

One or more detectors may be configured to measure a property of the four components such as intensity. The four intensities may be used to correct for an undesired tilt and/or to control a correct alignment.

In a further embodiment of the invention, the first part and the second part are coupled via at least one layer present in between. The layer can be designed to approximately equalize the transmission and reflection coefficient as required.

In yet another embodiment of the invention, at least one of the at least one layer includes air. A layer of air may reduce the amount of mechanical contact between the two parts of the optical component.

In a further embodiment of the invention, the ellipsometer further includes at least one grating, which is configured to transmit at least one of the beam and the four components. Such an arrangement may be applied to make broadband measurements feasible.

While specific embodiments have been described above, it will be appreciated that the invention may be practiced otherwise than as described. In addition, embodiments also include computer programs (e.g. one or more sets or sequences of instructions) to control a lithographic apparatus to perform a method as described herein, and storage media (e.g. disks, semiconductor memory) storing one or more such programs in machine-readable form. The description is not intended to limit the invention.

What is claimed is:

1. An ellipsometer comprising:
   an optical component including a first birefringent part and a second birefringent part, said first birefringent part having a first optical axis oriented along a first direction and being connected along a border surface to said second birefringent part, said second birefringent part having a second optical axis oriented along a second direction different from said first direction; and
   at least one detector,
   wherein said optical component is configured to receive a beam of radiation having a state of polarization, and
   wherein said border surface is configured to split said beam into first and second components reflected into said first birefringent part and third and fourth components transmitted into said second birefringent part, and
   wherein said at least one detector is configured to measure a property of at least three of said four components.

2. The ellipsometer according to claim 1, said ellipsometer comprising an evaluation unit configured to calculate said state of polarization based on the measured properties of said at least three components.

3. The ellipsometer according to claim 2, wherein said evaluation unit comprises a processor.

4. The ellipsometer according to claim 1, wherein said property is at least one of a phase and an intensity of said at least three components.

5. The ellipsometer according to claim 1, wherein said first birefringent part and said second birefringent part are connected via at least one layer present in between.

6. The ellipsometer according to claim 5, wherein said at least one layer includes a layer of material configured to equalize transmitted and reflected optical power.

7. The ellipsometer according to claim 5, wherein at least one of said at least one layer comprises air.

8. The ellipsometer according to claim 7, wherein said at least one layer of air has a thickness of about one-half of the wavelength of said radiation.

9. The ellipsometer according to claim 1, wherein said at least one optical component is shaped as a prism.

10. The ellipsometer according to claim 1, wherein, for each of the four components, said at least one detector is configured to measure at least one property of each of said four components, said at least one property being at least one of a group comprising an intensity and a phase.

11. The ellipsometer according to claim 1, further comprising at least one grating configured to transmit at least one of a group comprising said beam, a first of said four components, a second of said four components, a third of said four components, and a fourth of said four components.

12. A lithographic apparatus comprising an ellipsometer according to claim 1.

13. A measurement device comprising an ellipsometer according to claim 1 and a detection and evaluation unit configured to calculate said state of polarization.

14. A lithographic apparatus comprising a measurement device according to claim 13.

15. An ellipsometer according to claim 1, wherein said first direction is substantially parallel to a direction of propagation of said beam of radiation as received by said optical component.

16. An ellipsometer according to claim 1, wherein a principal wavelength of said beam of radiation is outside the visible range.

17. An ellipsometer according to claim 1, wherein said second birefringent part is aligned with respect to said first birefringent part such that one of the third and the fourth component has a direction of propagation substantially parallel to a direction of propagation of said beam of radiation as received by said optical component.

18. A method of measurement, said method comprising:
   directing a measurement beam of radiation along an optical axis of a first birefringent part to a border surface between the first birefringent part and a second birefringent part, said second birefringent part having an optical axis oriented along a different direction from the optical axis of the first birefringent part; and
   measuring a property of each of at least three components of a group comprising a first component of the measurement beam, a second component of the measurement beam, a third component of the measurement beam, and a fourth component of the measurement beam,
   wherein said first and second components are reflected from said border surface into said first birefringent part,
   wherein said third and fourth components are transmitted from said border surface into said second birefringent part, and
   supplying or making available the measured property of each of said at least three components for further analysis or processing.

19. The method of measurement according to claim 18, said method comprising calculating a state of polarization of the measurement beam based on the measured properties of said at least three components.

20. The method of measurement according to claim 18, wherein said measuring a property includes measuring at least one of a phase and an intensity of at least three components in said group.

21. The method of measurement according to claim 18, wherein said border surface includes a partially reflective coating.

22. The method of measurement according to claim 18, wherein said border surface includes a layer of air.

23. The method of measurement according to claim 18, wherein said measuring a property includes measuring an intensity of each of said first, second, third, and fourth components.

24. The method of measurement according to claim 18, wherein a principal wavelength of said measurement beam is outside the visible range.

25. The method of measurement according to claim 18, wherein a direction of propagation of said third component is substantially parallel to the optical axis of the first birefringent part.

26. The method of measurement according to claim 18, said method comprising determining a complex reflectivity of a surface of a substrate based on a result of said detecting a property.

27. The method of measurement according to claim 26, wherein said directing said measurement beam of radiation includes receiving the measurement beam as a reflection from the surface of the substrate.

28. The method of measurement according to claim 18, said method comprising:
 patterning a beam of radiation, and
 projecting the patterned beam onto a target portion on a surface of a substrate,
 wherein said projecting is based on a result of said measuring a property.

29. The method of measurement according to claim 28, wherein said directing includes receiving the measurement beam as a reflection from the surface of the substrate.

30. An ellipsometer comprising:
 a first birefringent part;
 a second birefringent part; and
 at least one detector,
 wherein said first and second birefringent parts are arranged in optical communication via a border surface such that a beam of radiation transmitted through said first birefringent part is split into a first component, a second component, a third component, and a fourth component, said first and second components being reflected from said border surface into said first birefringent part and said third and fourth components being transmitted from said border surface into said second birefringent part,
 and wherein said at least one detector is configured to measure a property of each of at least three of the first, second, third and fourth components.

31. The ellipsometer according to claim 30, wherein said first birefringent part has an optical axis oriented in a first direction, and
 wherein said second birefringent part has an optical axis oriented in a second direction different from said first direction.

32. The ellipsometer according to claim 30, wherein said border surface includes a partially reflective coating.

33. The ellipsometer according to claim 30, wherein said first birefringent part is configured to be moveable with respect to said second birefringent part to adjust a distribution of power among at least two of the first, second, third, and fourth components.

* * * * *